(12) United States Patent
Wright et al.

(10) Patent No.: US 7,802,485 B2
(45) Date of Patent: Sep. 28, 2010

(54) ATMOSPHERIC SAMPLING APPARATUS WITH FLEXIBLE LINE AND PROBE

(75) Inventors: James E. Wright, Pittsburgh, PA (US); Daniel J. Rybarski, Algonquin, IL (US); Volker Schmid, Pittsburgh, PA (US)

(73) Assignee: Clean Air Engineering, Inc., Pittsburgh, PA (US)

( * ) Notice: Subject to any disclaimer, the term of this patent is extended or adjusted under 35 U.S.C. 154(b) by 314 days.

(21) Appl. No.: 11/904,952

(22) Filed: Sep. 28, 2007

(65) Prior Publication Data

US 2009/0084198 A1 Apr. 2, 2009

(51) Int. Cl.
*G01N 1/10* (2006.01)

(52) U.S. Cl. ............... 73/863.85; 73/863.81; 73/863.11

(58) Field of Classification Search ............. 73/863.41, 73/863.11, 863.51, 863.81, 863.85
See application file for complete search history.

(56) References Cited

U.S. PATENT DOCUMENTS

| | | | |
|---|---|---|---|
| 3,727,029 A * | 4/1973 | Chrow ................. | 392/468 |
| 3,965,748 A * | 6/1976 | Boubel et al. ........... | 73/863.03 |
| 4,161,883 A | 7/1979 | Laird et al. | |
| 4,355,539 A | 10/1982 | Schatz | |
| 4,855,668 A | 8/1989 | Crow | |
| 5,109,711 A | 5/1992 | Wendt | |
| 5,381,511 A * | 1/1995 | Bahar et al. ............. | 392/472 |
| 5,499,528 A * | 3/1996 | Bahar .................. | 73/23.2 |
| 5,907,109 A * | 5/1999 | Tedeschi ............... | 73/864.73 |
| 5,918,256 A * | 6/1999 | Delaney ................ | 73/23.31 |
| 6,487,920 B1 | 12/2002 | Robbat, Jr. | |
| 6,516,676 B1 | 2/2003 | Mullowney, Jr. | |
| 6,857,327 B2 | 2/2005 | Silvis et al. | |
| 7,051,604 B1 | 5/2006 | Mayeaux | |

FOREIGN PATENT DOCUMENTS

JP 11094718 4/1999
JP 2000088837 3/2000

* cited by examiner

*Primary Examiner*—Hezron Williams
*Assistant Examiner*—Nashmiya S Fayyaz
(74) *Attorney, Agent, or Firm*—Olson & Cepuritis, Ltd.

(57) ABSTRACT

Arrangements for withdrawing carefully controlled samples from an active flue gas source are disclosed. A testing assembly is provided for connection to downstream processing equipment to obtain a sample from a gas stream. Included is a probe, a flexible sample line and a coupler joining the probe and the flexible sample line. At least one externally controlled or self-regulating heating cable is put in heating communication with the flexible line. A receptacle engaging the coupler is also provided for positioning the probe with respect to the flue gas source.

9 Claims, 6 Drawing Sheets

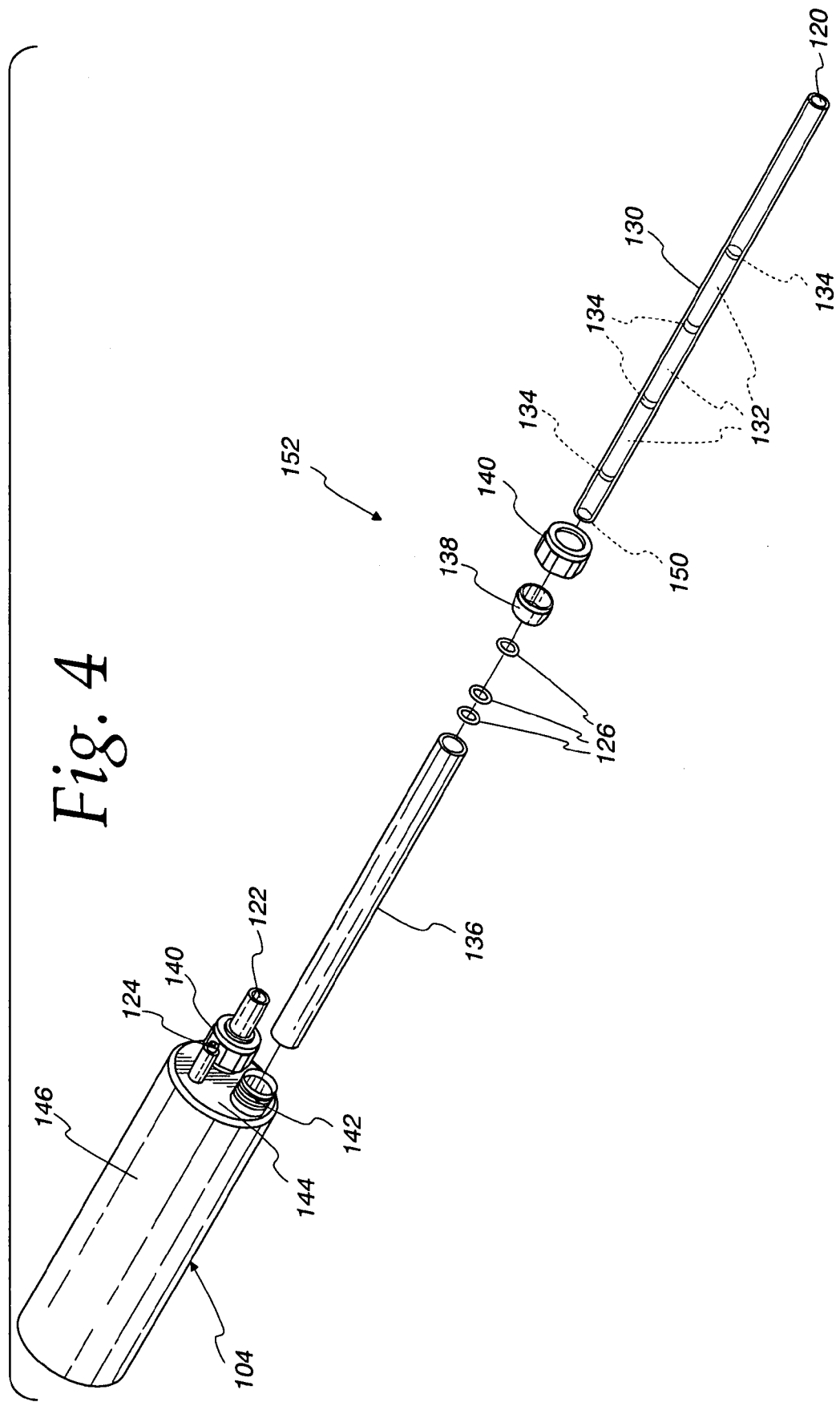

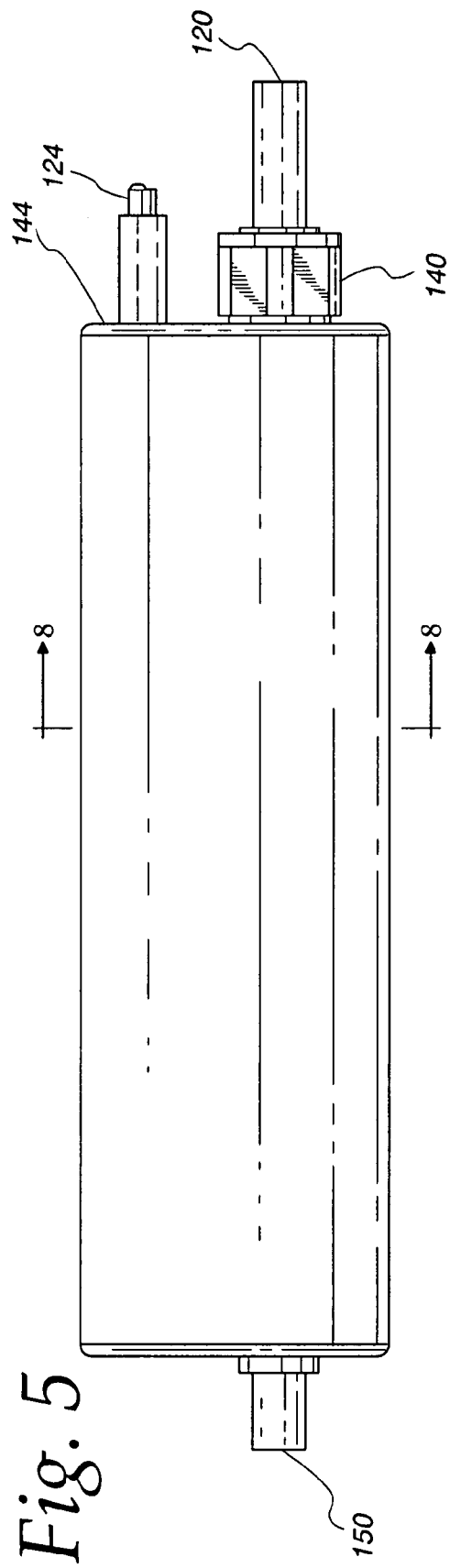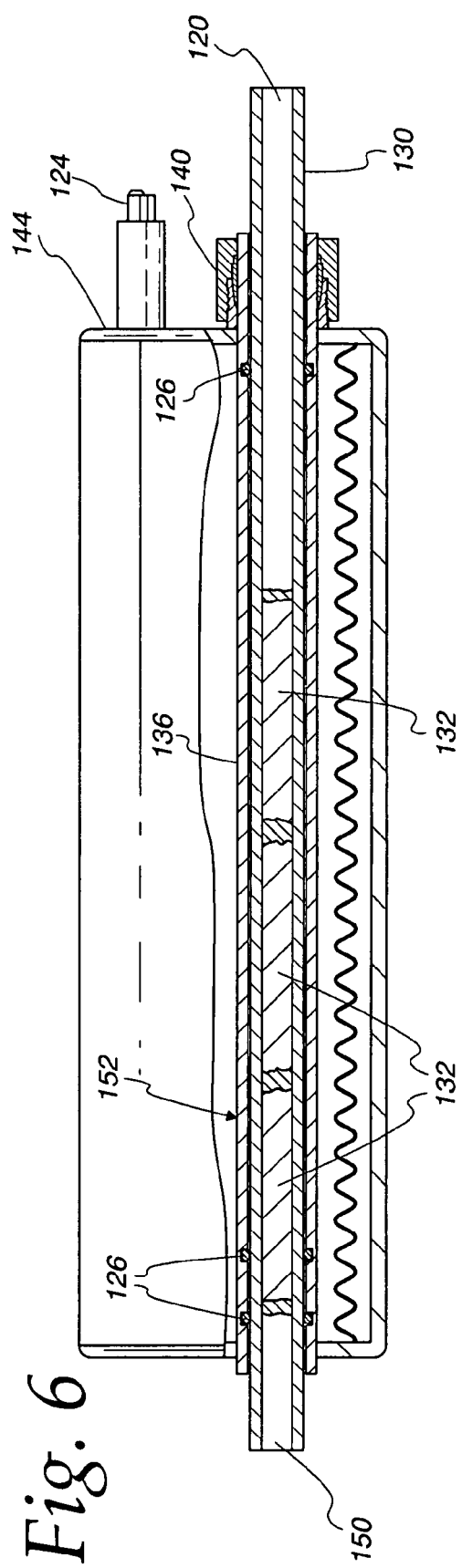

ATMOSPHERIC SAMPLING APPARATUS WITH FLEXIBLE LINE AND PROBE

FIELD OF THE INVENTION

The present invention relates to the testing of atmospheric emissions and, in particular, to testing equipment for withdrawing samples from a flue gas stream or other atmospheric discharge, especially on a continuous testing basis.

BACKGROUND OF THE INVENTION

Owners and operators of certain combustion devices are required to comply with a variety of environmental regulations pertaining to the maximum allowable emissions of a particular substance. One example of such regulations is directed to the concentration of a substance suspended in a waste gas, such as the flue gas of a combustion device, that discharges a waste gas stream into the atmosphere. In addition to specifying maximum allowable amounts or concentrations, environmental regulations at times specify how a waste gas stream is to be tested in order to determine regulatory compliance. Taking into account the different technologies and characteristics of substances involved, different testing techniques are often required for different types of substances, and additionally for different timing of such testing. For example, testing can be periodic or continuous.

One example of continuous emission monitoring regulations is found in part 75 of Title 40 of the Code of Federal Regulations, which pertains to the protection of the environment by way of continuous emission monitoring. Subpart I of these regulations is concerned with the continuous emission monitoring of mercury mass emissions of certain coal-fired units. Included in the regulations is a requirement as to how certain aspects of the continuous emission monitoring are to be carried out.

Compliance may be audited by a site visit for testing purposes, or a continuous monitoring program may be required. In either event, testing can require a substantial investment in capital and man-hours. Improvements in testing equipment, especially for repetitive (e.g. continuous) testing are continually being sought.

SUMMARY OF THE INVENTION

The present invention provides a novel and improved arrangement for withdrawing carefully controlled samples from an active flue gas source. Equipment provided by the present invention allows easy withdrawal of the sample material, while leaving associated equipment, such as vacuum pumps and line heaters, undisturbed. The present invention minimizes the disadvantages associated with prior art devices and materials related thereto.

One embodiment comprises a testing assembly for connection to downstream processing equipment to obtain a sample from a gas stream. Included is a probe having a first end with a gas inlet and a second end, a flexible sample line and a coupler joining the second end of the probe and the flexible sample line. The flexible sample line includes at least one gas channel comprising a flexible gas line coupled to the probe to transmit a sample from the probe inlet to the downstream processing equipment. At least one externally controlled or self-regulating heating cable is put in heating communication with the flexible line. The flexible sample line further includes an outer sheath surrounding the flexible gas line and the heating cable, and a thermal insulator is disposed within the outer sheath and surrounds the flexible line and the heating cable.

In another embodiment, a system for controlled positioning of a probe with respect to a gas stream is provided wherein the probe has a first end with a gas inlet and a second end for connection to downstream processing equipment to deliver a sample from the gas stream. Included is a flexible interconnect for connecting the probe to the downstream processing equipment, and a coupler for joining the second end of the probe and the flexible interconnect. The flexible interconnect includes at least one gas channel comprising a flexible gas line coupled to the probe to transmit a sample from the probe inlet to the downstream processing equipment. At least one externally controlled or self-regulating heating cable is put in heating communication with the flexible line. The flexible interconnect further includes an outer sheath surrounding the flexible gas line and the heating cable. A thermal insulator is disposed within the outer sheath and surrounds the flexible line and the heating cable. A receptacle for receiving the probe and the coupler includes a lever operated cam spaced a predetermined distance from the gas stream and engaging the coupler so as to position the gas inlet of the probe with a preselected relationship to the gas stream.

In a further embodiment, a flexible interconnect is provided for connecting a probe having a first end with a gas inlet and a second end, to downstream processing equipment to obtain a sample from a gas stream. Included is a coupler for joining to the second end of the probe, at least one gas channel comprising a flexible gas line having an inlet end for coupling to the probe, to transmit a sample to downstream processing equipment, and at least one externally controlled or self-regulating heating cable in heating communication with the flexible line. An outer sheath surrounds the flexible gas line and the heating cable, and a thermal insulator is disposed within the outer sheath so as to surround the flexible gas line and the heating cable.

BRIEF DESCRIPTION OF THE DRAWINGS

In the drawings:

FIG. 4 is an exploded perspective view thereof;

FIG. 5 is a side elevational view thereof;

FIG. 6 is a side elevational view thereof shown partly broken away;

DESCRIPTION OF THE PREFERRED EMBODIMENT

Figure 1:
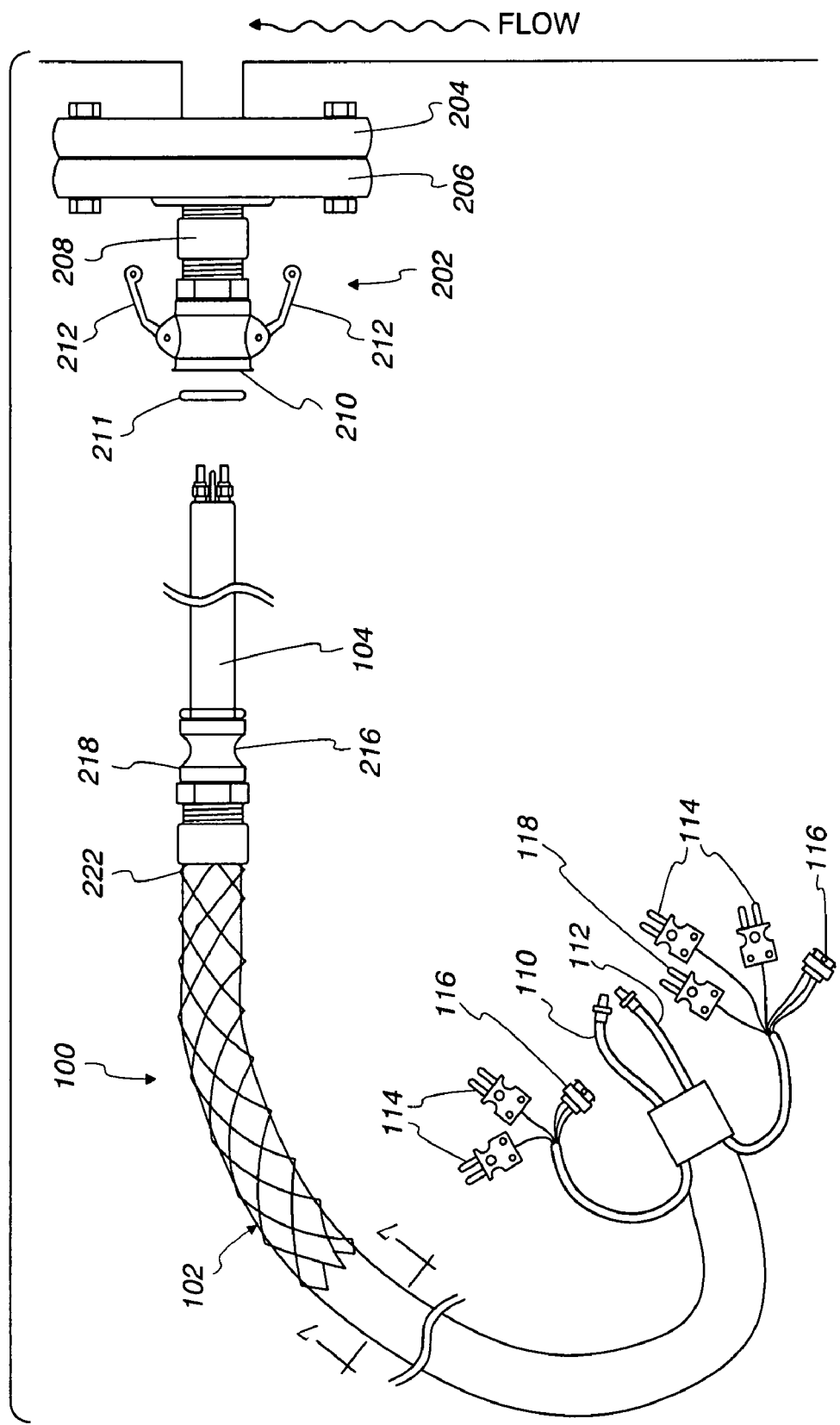
FIG. 1 is a schematic diagram of a testing system employing the present invention.

The invention disclosed herein is, of course, susceptible of embodiment in many forms. Shown in the drawings, and described herein in detail, is a preferred embodiment of the invention. It is understood, however, that the present disclosure is an exemplification of the principles of the invention and does not limit the invention to the illustrated embodiment.

For ease of description, a system for testing a gas stream such as a combustion flue gas stream embodying the present invention is described herein in its usual assembled position as shown in the accompanying drawings and terms such as upstream, downstream, inner, outer, upper, lower, horizontal, longitudinal, etc., may be used herein with reference to this usual position. However, the system may be manufactured, transported, sold or used in orientations other than that described and shown herein.

Flue gas sampling is one example of many industrial applications where it is necessary to maintain the physical and chemical integrity of a gas sample extracted from a process stream. Frequently, the temperature of the sampled gas must be maintained above a critical lower temperature while it is being transported through sampling lines to downstream measuring devices and other equipment, in order to avoid condensation or otherwise altering important properties of the gas sample.

Conventional gas sample extraction systems are known to include a sample probe to be inserted directly into a process stream, such as the flue gas stream of a smokestack. A heated sample line is provided to transport the sample to downstream equipment. In many applications, gas sampling systems must be carefully constructed from non-reactive materials capable of sustaining elevated temperatures. However, certain problems have been noted in the use of conventional equipment. For example, the junction where the sample probe and sample transport line are connected must be maintained at an elevated temperature and must be free of leaks, either entering or leaving the gas sample system. The junction is typically embodied in a junction box, in order to meet demanding criteria, such as the criteria discussed herein.

Referring now to the drawings, and initially to FIG. 1, a testing assembly is generally indicated at 100. Included is a flexible sample line 102 and a generic probe 104. If desired, probe 104 and sample line 102 could be made to carry only a single sampling channel. However, in the preferred embodiment, sample line 102 and probe 104 have the capacity to carry multiple separate, independent sampling channels, and are thus referred to herein as a multi-channel sample line and a multi-channel probe, respectively. As can be seen in FIG. 1, the sample line 102 and probe 104 are joined, preferably permanently joined, so as to form a single unitary testing assembly.

Probe 104 and sample line 102 preferably have multiple separate and independent gas sampling channels. In the preferred embodiment, the gas sampling channels include tubing of flexible, non-reactive material such as TEFLON or other engineered fluoropolymeric material. The flexible lines are indicated in FIG. 1 at 110, 112. Also included are connectors for a variety of auxiliary equipment such as sensors and heaters. Included are connectors 114, 116 associated with each flexible line and a connector 118 associated with instrumentation separate from the flexible lines.

Figure 2:
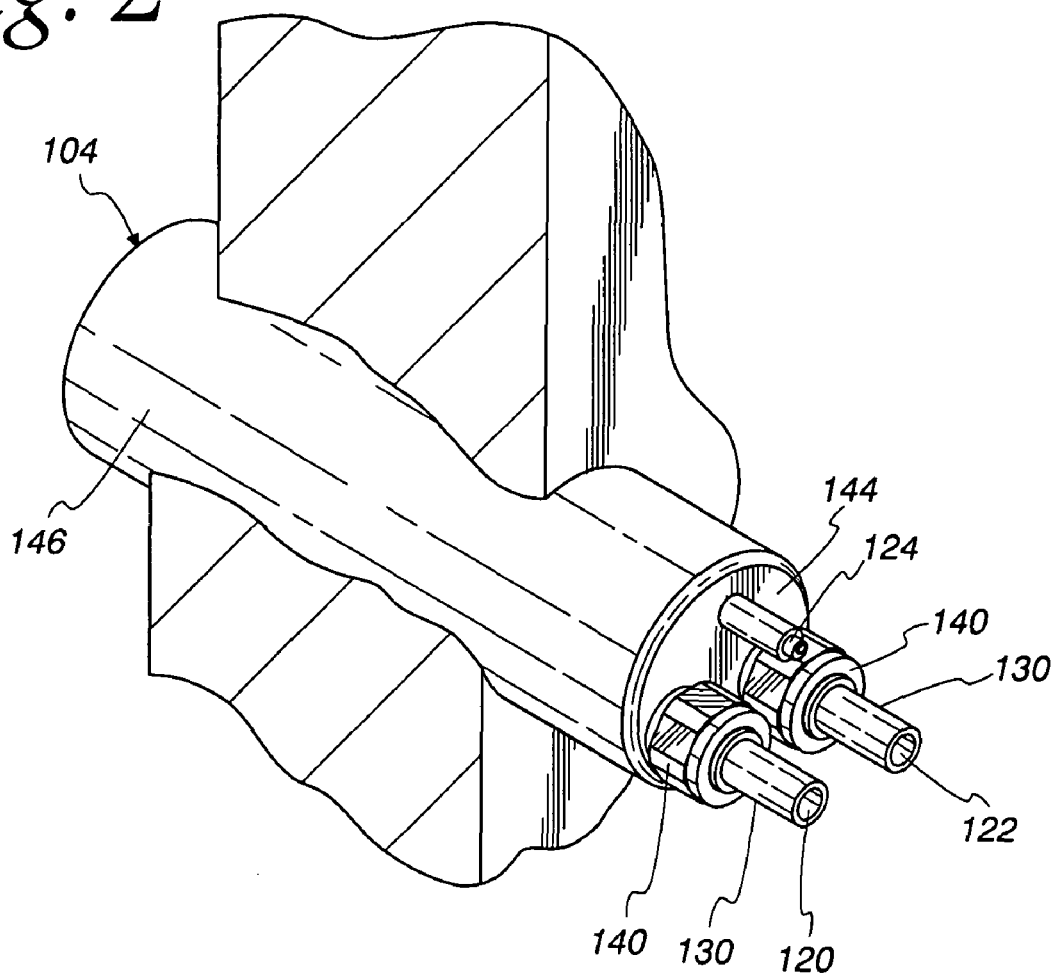
FIG. 2 is a schematic perspective view of a multi-channel probe shown installed in a flue gas stream.
Figure 3:
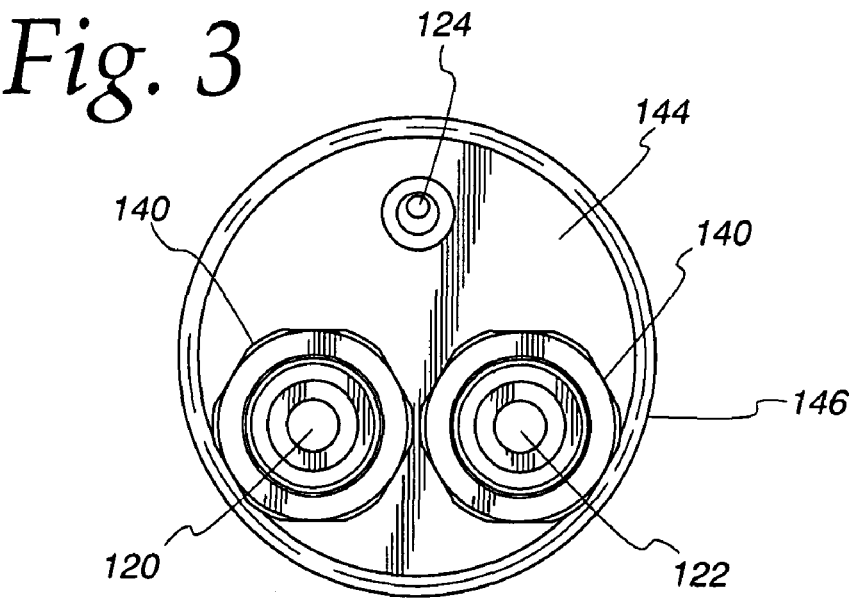
FIG. 3 is an end view thereof.

Probe 104 can comprise virtually any type of probe known today, having either single or multiple channel capability. As mentioned, in a preferred embodiment, probe 104 has multi-channel gas sampling capability and includes a pair of gas sampling channels. Referring to FIG. 2, the gas sampling channels have inputs 120, 122. A thermocouple 124 is also located adjacent gas inputs 120, 122. In the preferred embodiment, probe 104 is designed to have a specialized gas sampling capability, to withdraw gas samples using absorbent material. In a preferred embodiment, probe 104 utilizes sorbent trap technology.

Referring briefly to FIG. 4, included in probe 104 is a sorbent trap 130 with an insert including sections 132 of sorbent trap material. Although not required, the sorbent trap insert 130 is received within an outer shell 136 of rugged stainless steel construction. A ferrule or frustoconical collar 138 is attached, preferably by welding or brazing, to the inlet end of shell 136, and a nut or compression fitting 140 that threadingly engages a threaded nipple 142 which is fitted to an end cap 144 of a rugged stainless steel housing 146 of probe 104. In a preferred embodiment, the compression fitting 140 can be removed for ready withdrawal of a sample cartridge 152 formed by the combination of sorbent trap insert 130, outer shell 136 and, as an option, fitting 140. The sorbent trap insert 130 may be easily withdrawn from shell 136 with the shell 136 either removed from housing 146 or left in place as shown, for example, in the adjacent gas sampling channel having input 122. However, virtually any sample probe arrangement can be utilized with the present invention and removable inserts and/or removable cartridge assemblies are not required.

Referring to FIGS. 5 and 6, the downstream ends 150 of the sorbent trap inserts 130 are coupled to flexible lines 110, 112 (see FIG. 1) in a manner (not shown) to form a continuous gas sampling passageway. As will be seen herein, auxiliary equipment such as thermocouples and heaters are combined with the gas passageways to form a pair of gas sampling channels.

Figure 7:
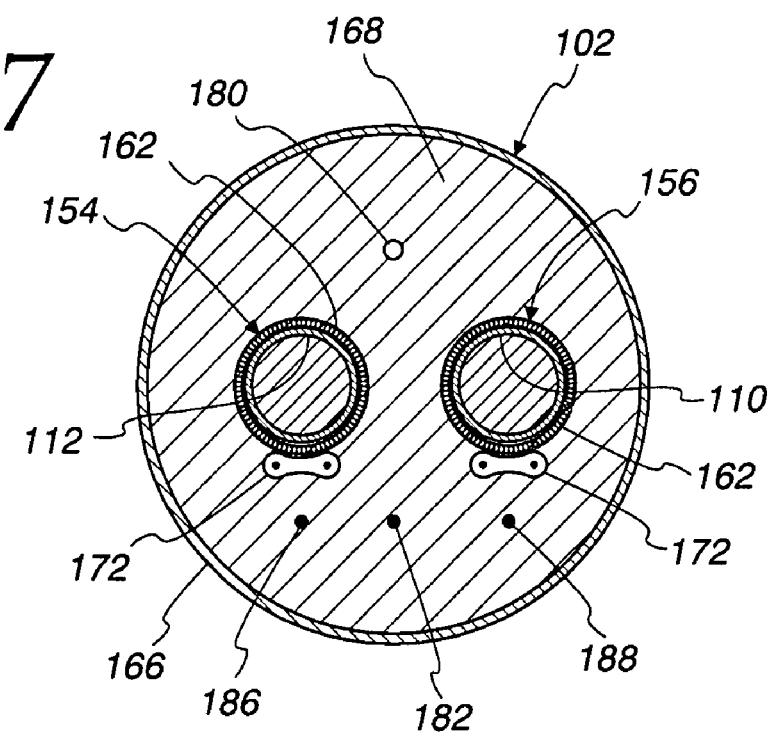
FIG. 7 is a cross-sectional view taken along the line 7-7 of FIG. 1.

Referring now to FIG. 7, a cross-sectional view of sample line 102 is shown. Included in the sample line 102 are two gas sampling channels generally indicated at 154, 156. Included in each channel are flexible hollow lines 110, 112 which, as mentioned above, are preferably made of TEFLON material. Surrounding the flexible lines 110, 112 is an outer covering 162 of thermal barrier material such as fiberglass cloth, which is coated, wrapped or otherwise disposed about each flexible line. As indicated in FIG. 7, the channels 154, 156 are spaced apart and disposed within a rugged outer weatherproof jacket 166 of polyurethane material. The outer jacket 166 is preferably formed with a shrink-wrap process. The interior of sample line 102 is filled with a thermal insulator material such as glass fiber insulation and most preferably non-hygroscopic glass fiber insulation material indicated at 168.

Also included in each gas channel is a externally controlled or self-regulating heater preferably in the form of electrical cables schematically indicated at 172. Preferably, each flexible line is wrapped with two independent externally controlled or self-regulating electric resistance cable heaters. The length of the first heater cable is equal to the length of the flexible line that is inserted into the process stream. The second heater cable is wrapped around the length of flexible line that remains outside of the process stream. As indicated in FIG. 7, the heater cables are encapsulated in insulation material 168. In the preferred embodiment, the two heaters for each gas channel provide an arrangement for maintaining two temperature zones. One zone is the section of the sample line that is covered by the probe sheath or outer probe housing 146. This section is exposed to the process gas and must maintain the proper sample gas temperature while being exposed to the temperature of the process gases. The second heated zone is the section of the flexible line that transports the extracted sample to downstream equipment such as a gas conditioning and pumping system of the type generally indicated in FIG. 9 to be discussed below. The second heated zone maintains the proper gas temperature while being exposed to ambient air temperature.

The section of the sample line 102 that is inserted into the process stream is wrapped with a high temperature protective jacket of silicone material. This section is placed inside the rigid stainless steel tube forming the outer housing 146, shown in FIG. 4. As mentioned, the housing 146 at the free end of the probe is joined to an end wall 144, preferably by welding, brazing, or other metallurgical joiner. That portion of sample line 102 that remains outside of the process gas is wrapped with the weatherproof protective jacket 166 (see FIG. 7).

In a preferred embodiment, sample line 102 contains instrumentation for the operation of the testing assembly. Included are a number of thermocouples measuring different operating parameters. The thermocouples are accessed by connectors 114, 118 shown in FIG. 1. Referring again to FIG. 7, a line thermocouple 180 is provided to measure the internal temperature of sample line 102. As mentioned with reference to FIG. 2, a thermocouple 124 is provided for sensing the temperature of the process gas and is placed in-situ in the gas stream adjacent gas inlets 120, 122. The signal for this thermocouple is carried by electrical conductor 182 shown in FIG. 7. Connection with the thermocouple is made with connector 118 in FIG. 1. As mentioned, the sorbent trap inserts 130 are located in probe 104. Preferably, the temperature of the sorbent traps are monitored by their own respective thermocouples, with signals being transmitted through electrical conductors 186, 188 to a pair of connectors 114 as shown in FIG. 1.

Figure 8:
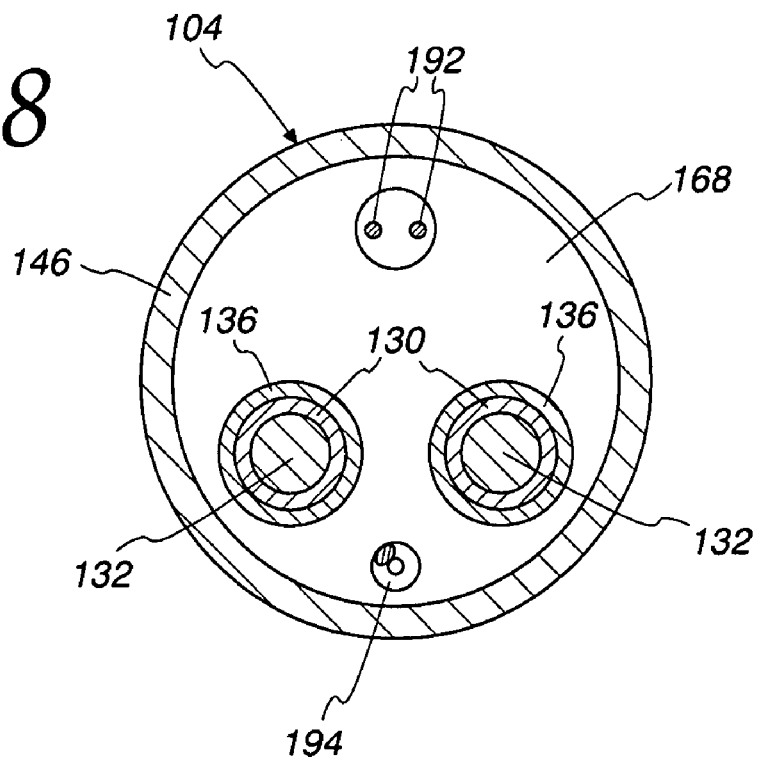
FIG. 8 is a cross-sectional view taken along the line 8-8 of FIG. 5.

Referring now to FIG. 8, a section of probe 104 is shown schematically in cross-section. Included are the sorbent trap inserts 130, preferably in the form of hollow glass tubes receiving sections of sorbent trap material 132, separated from one another by separator sections 134 as shown for example in FIG. 4. Referring again to FIG. 8, the outer shell 136 of the sorbent trap cartridge surrounds the sorbent trap inserts 130. Electrical conductors 192 for thermocouple 124 are located in the upper portion of FIG. 8 and electrical conductors 194 are provided for additional instrumentation. The interior of the probe is filled with thermal insulation which, as mentioned, preferably comprises non-hygroscopic glass fiber insulation. As shown in FIGS. 7 and 8, is the outer jacket 166 is preferably located immediately inside of the rigid, stainless steel housing 146.

There are many applications involving the direct insertion of sorbent traps into an industrial gas stream to measure properties of the gas stream. One application, for example, requires the measurement of a trace component, such as mercury concentrations, using sorbent traps. Sorbent traps may include, for example, glass tubes packed with iodinated activated carbon. As mentioned in greater detail herein, one protocol for this measurement is contained in the alternative mercury monitoring approach detailed in 40 C.F.R. 75, Appendix K.

Usually, sorbent trap sampling requires forming and maintaining a gas-tight seal between the traps and the physical device used to hold them in place during sampling, herein referred to as a sorbent trap module or probe. This arrangement allows a vacuum to be placed on the apparatus during sampling and any leakage between the trap and the apparatus could lead to erroneous sampling results. For example, in Appendix K applications, the gas seal, such as that provided by the present invention must be able to maintain leak tightness at a minimum vacuum of 15 inches Hg absolute pressure. Additionally, the seal provided by the present invention is able to withstand chemical and physical conditions of the environment inside the gas stream which, as will be apparent to those skilled in the art, may often times be hot, corrosive and/or dust-laden.

Sorbent trap modules or probes according to principles of the present invention allow sorbent trap inserts to be quickly inserted and removed from the probe without the use of tools. The trap or insert is pushed by hand into a removable module inside the probe, preferably in the form of cartridge 152 shown for example in FIG. 6. A leak-tight seal is made between the insert 130 and the shell 136 of cartridge 152 by a series of three o-rings 126, preferably contained within interior grooved rings formed inside of cartridge shell 136 in the manner indicated in FIG. 1. The probe 104 and cartridge 152 preferably include outer housings made of stainless steel or another type of corrosion-resistant ridged material. Preferably, the o-rings 126 are made of a pliable, chemically resistant and thermally stable polymer such as silicone or VITON. The cartridges 152 are held in place within the probe and sealed to the probe using a threaded compression fitting and nut assembly 142, 138 and 140, respectively.

Accordingly, the sorbent traps, i.e., sorbent trap inserts 130 can be inserted and removed without the need for tools such as wrenches or pliers. With the present invention, the sampling process is simplified and is made more time efficient. The sorbent trap module or cartridge 152 can be readily removed from probe 104 and replaced with a new one, as may be desired. The nut 140 used to hold the cartridge in place within probe 104 may be tightened and loosened with a wrench, but, according to a preferred embodiment, the cartridge 152 is not removed from the probe 104 except for periodic maintenance purposes, such as o-ring wear. In this regard, it is generally preferred in the present invention that three o-rings are provided to seal the sorbent trap insert 130 and to provide redundancy in case of failure of a particular o-ring. Further, as can be seen for example in FIG. 1, it is generally preferred that two o-rings be placed close to each other at the downstream end 150 of the sorbent trap insert and that a single o-ring be located at the forward or free end of probe 104, adjacent the gas inlet end 120 of the sorbent trap insert.

With reference to FIG. 6, the test assembly 100 conveniently provides a multichannel, redundant testing capability which is often a condition for a regulatory body to allow self-testing programs implemented by the facility operator, rather than a designee or member of the responsible agency. In order to provide maximum benefits to an operator, the testing assembly should be relatively lightweight and for the most part reusable from one testing operation to another. This is particularly important where continuous or quasi-continuous monitoring is required. Several times a day, during continuous operation of the facility, examples are withdrawn from the gas stream, an operation often repeated during the life of the facility, especially since many large scale facilities are seldom completely shut down.

As mentioned above, the probe 104 is preferable made rigid and with locating fitting 218, allows the accurate positioning of inlets for the gas sample channels within the gas stream flow to be tested. However, in light of the need for gas-tight seals to be continuously maintained during testing and the need for flexibility to allow the probe to be permanently joined to the sample line 102, it is important that the sample line be made relatively flexible, without compromising leak-free integrity of the test assembly. The preferred construction described above with reference to FIG. 7, for example, allows sample line 102 to meet these criteria while being relatively lightweight. The materials and dimensions of one example of a testing assembly have been given herein and afford a relatively lightweight construction, typically on the order of three pounds per linear foot.

With testing assemblies according to principles of the present invention, the exposed portions of the trap inserts, at the inlet to the gas channels, may be carefully controlled and protected by an operator from accidental contact and breakage, when contacting a nearby object. It should be remembered, in this regard, that often testing facilities are not typically provided for during design and construction of the facility but rather are added later, where space and other conditions allow. Further, testing operations are conducted, in many instances, continuously, year-round. In very cold weather when gloves and other protective apparel are required, the ability to control the free end of probe 104 and the exposed glass tubes projecting therefrom, becomes even more important. The flexible sample line 102, the construction of the rigid probe 104, the precision positioning fitting 218 and the receptacle construction 202 all contribute to ensure that continuous testing programs and other testing procedures can be successfully carried out, even during extreme atmospheric conditions.

The testing assembly according to the principles of the present invention provides a compact, relatively lightweight arrangement which aids in obtaining gas samples in difficult work areas of restricted accessibility such as may be provided about a smokestack of an operating combustion facility. For example, in one preferred embodiment according to the present invention, the outer housing 146 of probe 104 has a 2.5 inch outer diameter and sample line 102 has an outer diameter of similar dimensions. The sorbent trap inserts 130 are made of hollow glass tubing having an outer diameter of about 0.39 inches and an inside diameter of approximately 0.32 inches. The walls of outer shell 136 of the cartridge 152 preferably have a thickness of approximately 0.09 inches and a length of approximately 8.5 inches. The flexible lines 110, 112 preferably have an approximate nominal external diameter of approximately one quarter inch.

Turning again to FIG. 1, a fitting assembly generally indicated at 202 is provided for support and control of depth insertion of the probe in the process stream. Included in assembly 202 is a port 204 and flange 206. Connected to flange 206 is a pipe nipple 208 which preferably has a nominal internal diameter of 2.5 inches. Also included is a quick lock fitting 210 with an internal bore of approximately 2.5 inches, dimensioned to receive probe 104. A pair of cam locks (not shown) protrude into the inner bore of fitting 210 and are operated by lever arms 212. The cam members seat against a grooved portion 216 of a fitting 218 mounted at one end of probe 104 and are preferably rigidly connected thereto by welding, brazing or other form of metallurgical joinder. A flexible, high-temperature o-ring 211 (e.g., Viton) sits in a groove within the fitting 210 and seals against fitting 218 when the cam locks are engaged.

Fitting 218 is in turn connected to sample line 102 and a strain relief system 222 is provided to transfer support load to assembly 202. In operation, probe 104 is inserted into fitting 210 so as to project into the process flow in the manner indicated in FIG. 2. Preferably, fitting 218 provides an approximate insertion limit by engagement with fitting 210. The final insertion control is provided when the cam locks are operated by lever arms 212 with the cam locks received in groove 216 to provide a final, rigidly secure and accurately positioned engagement of the probe with respect to the process stream.

Although a particular probe construction has been described above, the testing assembly according to principles of the present invention can readily employ probes of different constructions and operating principles. Further, those skilled in the art will readily appreciate that the sample line can be readily modified to accommodate different numbers of gas channels to be monitored. For example, a single channel can be readily provided as can a system having three or more gas channels. Further, the present invention can be employed to test virtually any type of material.

Figure 9:
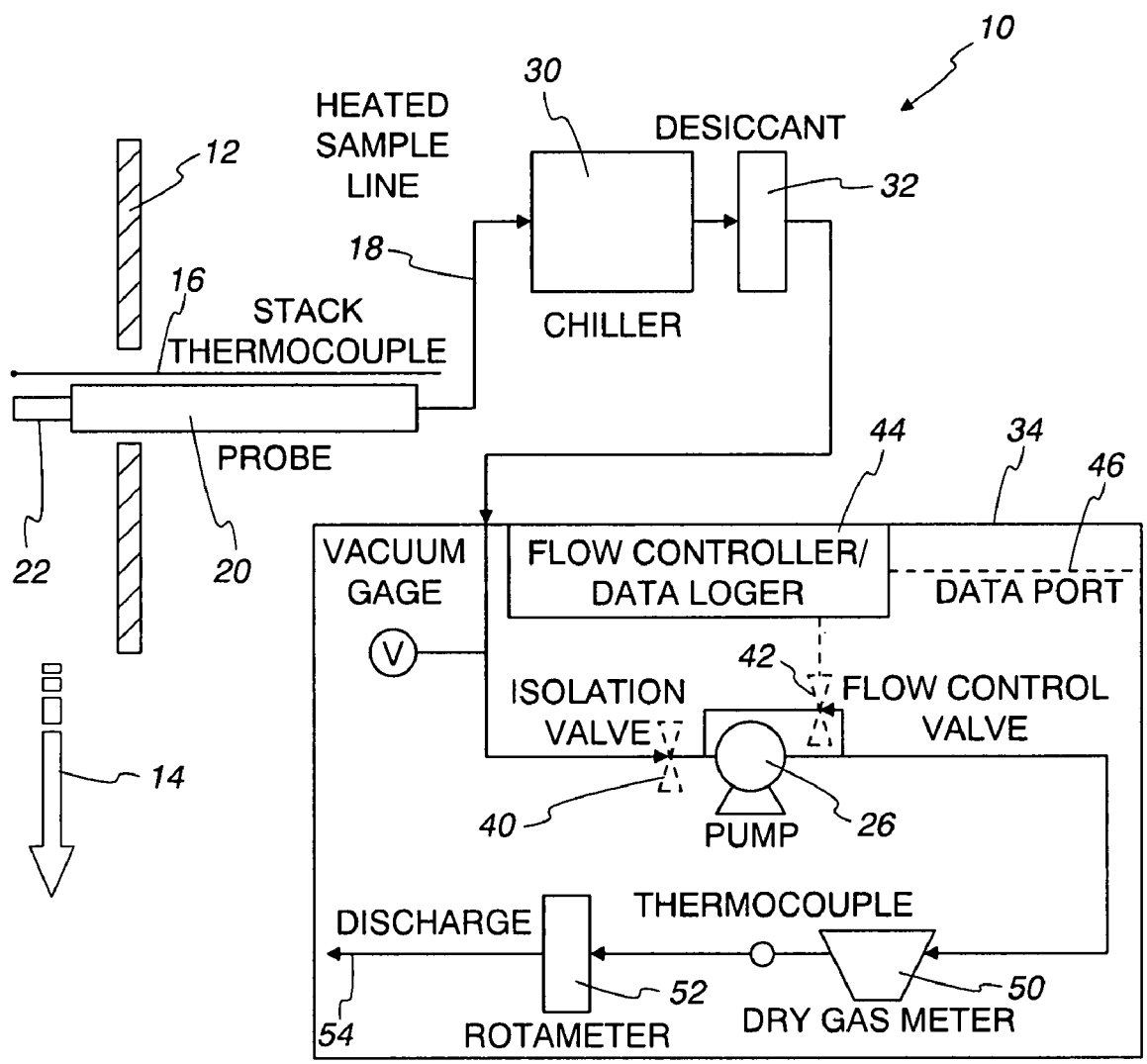
FIG. 9 is a schematic diagrammatic representation of a testing system.

Referring now to FIG. 9, a sample system suitable for use with the aforementioned probe, sample line and related equipment is generally indicated at 10. Included is a duct wall 12 confining a gas stream which flows in the direction of arrow 14. An entrance 16 formed in duct wall 12 is provided for probe 20. In one example, probe 20 includes a sorbent trap 22 which is placed in the gas stream. A pump 26 draws flue gas through trap 22 and probe 20. That portion of the gas stream passing through trap 22 is drawn through a chiller 30 and desiccant unit 32 before entering subsystem 34 which includes pump 26. An isolation valve 40 and flow control valve 42 are provided along with a flow controller/data logger 44 which outputs data on port 46. Gas stream leaving pump 26 passes through dry gas meter 50 and a rotating meter device 52 before being discharged at 54.

The foregoing descriptions and the accompanying drawings are illustrative of the present invention. Still other variations and arrangements of parts are possible without departing from the spirit and scope of this invention.

What is claimed is:

1. A system for controlled positioning of a probe with respect to a gas stream, the probe having a first end with a gas inlet and a second end for connection to downstream processing equipment to deliver a sample from the gas stream, comprising:
    a flexible interconnect for connecting the probe to the downstream processing equipment;
    a coupler for joining the second end of the probe and the flexible interconnect;
    the flexible interconnect including at least one gas channel comprising a flexible gas line coupled to the probe to transmit a sample from the probe inlet to the downstream processing equipment;
    at least one heating cable in heating communication with the flexible gas line;
    the flexible interconnect further including an outer sheath surrounding the flexible gas line and the heating cable;
    a thermal insulator disposed within the outer sheath and surrounding the flexible gas line and the heating cable; and
    a receptacle for receiving said probe and said coupler, including a lever operated cam spaced a predetermined distance from the gas stream and engaging said coupler so as to position the gas inlet of the probe with a preselected relationship to the gas stream.

2. The system according to claim 1 wherein the coupler has a position indexing surface located at a preselected distance from the gas inlet.

3. The system according to claim 2 wherein the coupler has an annular groove defining the position indexing surface.

4. The system according to claim 1 further comprising at least one instrumentation cable carried by the flexible interconnect.

5. The system according to claim 1 further comprising a first thermocouple in heat sensing communication with the probe and having output conductors carried by the flexible interconnect.

6. The system according to claim 5 further comprising a second thermocouple in heat sensing communication with the flexible gas line and having output conductors carried by a flexible sample line.

7. The system according to claim 6 further comprising a third thermocouple in heat sensing communication with the flexible interconnect and having output conductors carried by the flexible interconnect.

8. The system according to claim 1 wherein the probe has a plurality of gas inlets and the flexible interconnect has a plurality of gas channels coupled to the probe to transmit samples from the probe inlets to the downstream processing equipment.

9. The system according to claim 8 wherein the gas channels are spaced apart, one from the other.

* * * * *